US012667706B2

(12) United States Patent
Kuriyama et al.

(10) Patent No.: US 12,667,706 B2
(45) Date of Patent: Jun. 30, 2026

(54) FEMALE CONNECTOR

(71) Applicant: TERUMO KABUSHIKI KAISHA, Tokyo (JP)

(72) Inventors: Tasuku Kuriyama, Kai (JP); Toshihiko Kakinoki, Oyama (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 870 days.

(21) Appl. No.: 17/942,715

(22) Filed: Sep. 12, 2022

(65) Prior Publication Data

US 2023/0001175 A1 Jan. 5, 2023

Related U.S. Application Data

(63) Continuation of application No. PCT/JP2021/001262, filed on Jan. 15, 2021.

(30) Foreign Application Priority Data

Mar. 19, 2020 (JP) ................................. 2020-050034

(51) Int. Cl.
　*A61M 39/10* (2006.01)
　*A61M 39/04* (2006.01)
(52) U.S. Cl.
　CPC ........ *A61M 39/1011* (2013.01); *A61M 39/04* (2013.01); *A61M 2039/1077* (2013.01)
(58) Field of Classification Search
　CPC .. A61M 2039/1027; A61M 2039/1077; A61M 2039/1016; A61M 2039/1083;
(Continued)

(56) References Cited

U.S. PATENT DOCUMENTS

| | | | |
|---|---|---|---|
| 5,441,487 A | 8/1995 | Vedder | |
| 2008/0103487 A1* | 5/2008 | Miyasaka | A61M 39/26 604/537 |

(Continued)

FOREIGN PATENT DOCUMENTS

| | | |
|---|---|---|
| CN | 102015014 A | 4/2011 |
| JP | 2002-126094 A | 5/2002 |

(Continued)

OTHER PUBLICATIONS

International Searching Authority, "Written Opinion," issued in connection with International Patent Application No. PCT/JP2021/001262, dated Feb. 22, 2021 with English translation.
(Continued)

*Primary Examiner* — Kevin C Sirmons
*Assistant Examiner* — Alexandra Lalonde
(74) *Attorney, Agent, or Firm* — Foley & Lardner LLP

(57) ABSTRACT

A female connector configured to connect to a male connector comprising a lock claw and a channel connection portion having a hollow rod shape that defines a first channel therein, the female connector including: a cap; a housing; and a valve. The cap includes: a top wall comprising an opening, and a peripheral wall. The housing includes: a cylindrical wall having an inner peripheral surface that defines a second channel, and an engaging protrusion protruding from an outer peripheral surface of the cylindrical wall to form a lower surface configured to engage with the lock claw to connect the male connector to the female connector and put the male connector into a locked state. The valve includes: a sandwiched portion sandwiched between the top wall and the cylindrical wall, and a penetration portion located in the opening in a top view and penetrating the valve in an up-and-down direction.

9 Claims, 8 Drawing Sheets

<table>
<tr><td>JP</td><td>2013-529478 A</td><td>7/2013</td></tr>
<tr><td>JP</td><td>2013-252165 A</td><td>12/2013</td></tr>
<tr><td>JP</td><td>2018-007719 A</td><td>1/2018</td></tr>
</table>

(58) Field of Classification Search

CPC .. A61M 2039/1088; A61M 2039/1072; A61M 39/1011; A61M 39/04; A61M 39/10; A61M 39/26; A61M 39/105; A61M 2039/267; A61M 2039/1044; A61M 2039/0633; A61M 2039/0673; A61M 39/20; A61M 39/00; A61M 39/06; A61M 39/02; F16L 37/133; F16L 37/0985

See application file for complete search history.

(56) References Cited

U.S. PATENT DOCUMENTS

| | | | | |
|---|---|---|---|---|
| 2013/0079730 A1* | 3/2013 | Mosler | ................. | A61M 39/10 |
| | | | | 604/535 |
| 2015/0297830 A1* | 10/2015 | Okiyama | .............. | A61M 39/28 |
| | | | | 604/246 |

FOREIGN PATENT DOCUMENTS

| | | |
|---|---|---|
| JP | 2006-102254 A | 4/2006 |

OTHER PUBLICATIONS

Chinese Office Action dated May 29, 2025 in Chinese Appl. No. 202180006370.4.

Chinese Search Report dated May 26, 2025 in Chinese Appl. No. 202180006370.4.

International Searching Authority, "International Search Report," issued in connection with International Patent Application No. PCT/JP2021/001262, dated Feb. 22, 2021.

International Searching Authority, "Written Opinion," issued in connection with International Patent Application No. PCT/JP2021/001262, dated Feb. 22, 2021.

* cited by examiner

FEMALE CONNECTOR

CROSS-REFERENCE TO RELATED APPLICATIONS

This is a bypass continuation of PCT Application No. PCT/JP2021/001262, filed on Jan. 15, 2021, which claims priority to Japanese Application No. JP2020-050034, filed on Mar. 19, 2020. The contents of these applications are hereby incorporated by reference in their entireties.

BACKGROUND

This disclosure relates to a female connector.

In infusion, blood transfusion, and dialysis, medical tubes or the like are used to form a feeding line, and drug solutions, blood, and other fluids are delivered through this feeding line. Medical tubes, syringes, and other medical devices used in the feeding line are connected to each other using a connector set including a male connector and a female connector to which the male connector is connected (see, for example, JP 2013-252165 A).

The male connector includes a lock claw and a channel connection portion having a hollow rod shape that defines a first channel therein. The female connector includes a cap, a housing, and a valve. The cap includes a top wall provided with an opening that allows insertion of the channel connection portion of the male connector and a peripheral wall extending from an outer peripheral edge of the top wall. The housing includes a cylindrical wall having an inner peripheral surface that defines a second channel and an engaging protrusion protruding from an outer peripheral surface of the cylindrical wall to form a lower surface to be engaged with the lock claw to connect the male connector to the female connector and put the male connector into a locked state. The valve includes a sandwiched portion sandwiched between the top wall and the cylindrical wall and a penetration portion placed in the opening in a top view and penetrating the valve in up-and-down direction.

SUMMARY

In the aforementioned female connector in the related art, an outer peripheral surface of the peripheral wall of the cap and an outer peripheral surface of the engaging protrusion of the housing are flush with each other to enable smooth connection with the male connector. In other words, when the male connector is connected to the female connector, the lock claw sequentially and smoothly passes over the outer peripheral surface of the peripheral wall of the cap and that of the engaging protrusion of the housing to be engaged with the lower surface of the engaging protrusion.

In addition, in the female connector in the related art, a gap may be formed at a boundary between an upper surface of the engaging protrusion of the housing and a lower end face of the peripheral wall of the cap due to dimensional accuracy, assembly accuracy, and the like of each component. When the lock claw engaged with the lower surface of the engaging protrusion is unlocked by an unintended external force or the like, the lock claw is engaged with the gap. Because it is difficult to discern such an abnormal connected state by appearance, there is a possibility that the connectors are continued to be used in this state.

An object of this disclosure is to provide a female connector capable of smoothly connecting to a male connector and preventing a lock claw of the male connector from being engaged with a boundary between an engaging protrusion of a housing and a peripheral wall of a cap.

According to a first aspect of the disclosure, a female connector is connectable with a male connector including a lock claw and a channel connection portion having a hollow rod shape that defines a first channel therein, the female connector including: a cap; a housing; and a valve, the cap including a top wall provided with an opening configured to receive the channel connection portion and a peripheral wall extending from an outer peripheral edge of the top wall, the housing including a cylindrical wall having an inner peripheral surface that defines a second channel and an engaging protrusion protruding from an outer peripheral surface of the cylindrical wall to form a lower surface engaged with the lock claw to connect the male connector to the female connector and put the male connector into a locked state, and the valve including a sandwiched portion sandwiched between the top wall and the cylindrical wall and a penetration portion placed in the opening in a top view and penetrating the valve in up-and-down direction, in which the engaging protrusion and the peripheral wall form a boundary between an upper surface of the engaging protrusion and a lower end face of the peripheral wall, an outer diameter of the lower end face of the peripheral wall is less than an outer diameter of the upper surface of the engaging protrusion at the boundary, and the engaging protrusion has an outer peripheral surface including an enlarged diameter portion with a diameter increasing downward from the boundary.

According to an embodiment of the disclosure, the enlarged diameter portion has a tapered surface.

According to an embodiment of the disclosure, the peripheral wall has an outer peripheral surface including a fixed diameter portion having a constant outer diameter extending upward from the boundary.

According to an embodiment of the disclosure, the peripheral wall has an outer peripheral surface including a lower edge having a tapered surface or a protruding curved surface with a diameter that increases upward from the boundary.

According to an embodiment of the disclosure, the outer peripheral surface of the engaging protrusion has a fixed outer diameter over circumferential direction.

According to certain embodiments of the disclosure, there is provided a female connector capable of smoothly connecting to a male connector and preventing a lock claw of the male connector from being engaged with a boundary between an engaging protrusion of a housing and a peripheral wall of a cap.

DETAILED DESCRIPTION

Figure 1:
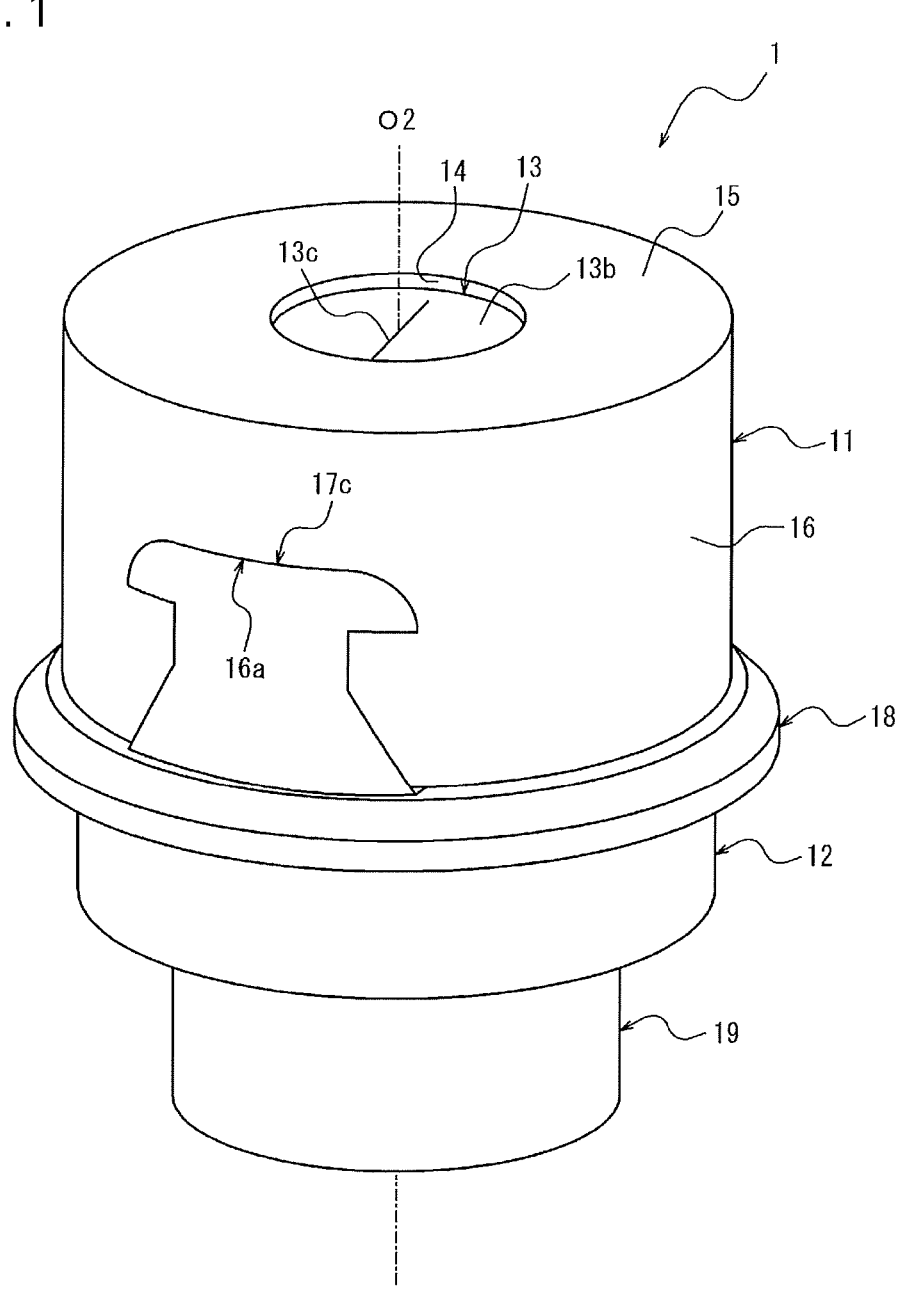
FIG. 1 is a perspective view of a female connector according to a first embodiment.

Hereinafter, a female connector according to an embodiment of this disclosure will be described in detail with reference to FIGS. 1 to 11. In the drawings, the same components are denoted with the same reference numerals.

With regard to a female connector 1 in each embodiment, a direction along a second axis O2, or the central axis of a peripheral wall 16 of a cap 11, is referred to as "up-and-down direction", a direction from a top wall 15 of the cap 11 toward a housing 12 along the second axis O2 (the lower side of FIG. 5) is referred to as "downward", the opposite direction is referred to as "upward", a direction around the second axis O2 is referred to as "circumferential direction", and a direction perpendicular to the second axis O2 is referred to as "radial direction". With regard to a male connector 2 in each embodiment, a direction along a first axis O1, or the central axis of a channel connection portion 4, is referred to as "up-and-down direction", a direction from a proximal end (base end) to a distal end of the channel connection portion 4 along the first axis O1 (the lower side of FIG. 5) is referred to as "downward", the opposite direction is referred to as "upward", a direction around the first axis O1 is referred to as "circumferential direction", and a direction perpendicular to the first axis O1 is referred to as "radial direction". The terms related to the up-and-down direction do not determine the orientation of the female connector 1 and the male connector 2 in use. For example, the female connector 1 and the male connector 2 may be used while the second axis O2 or the first axis O1 is perpendicular to the vertical direction.

Figure 2:
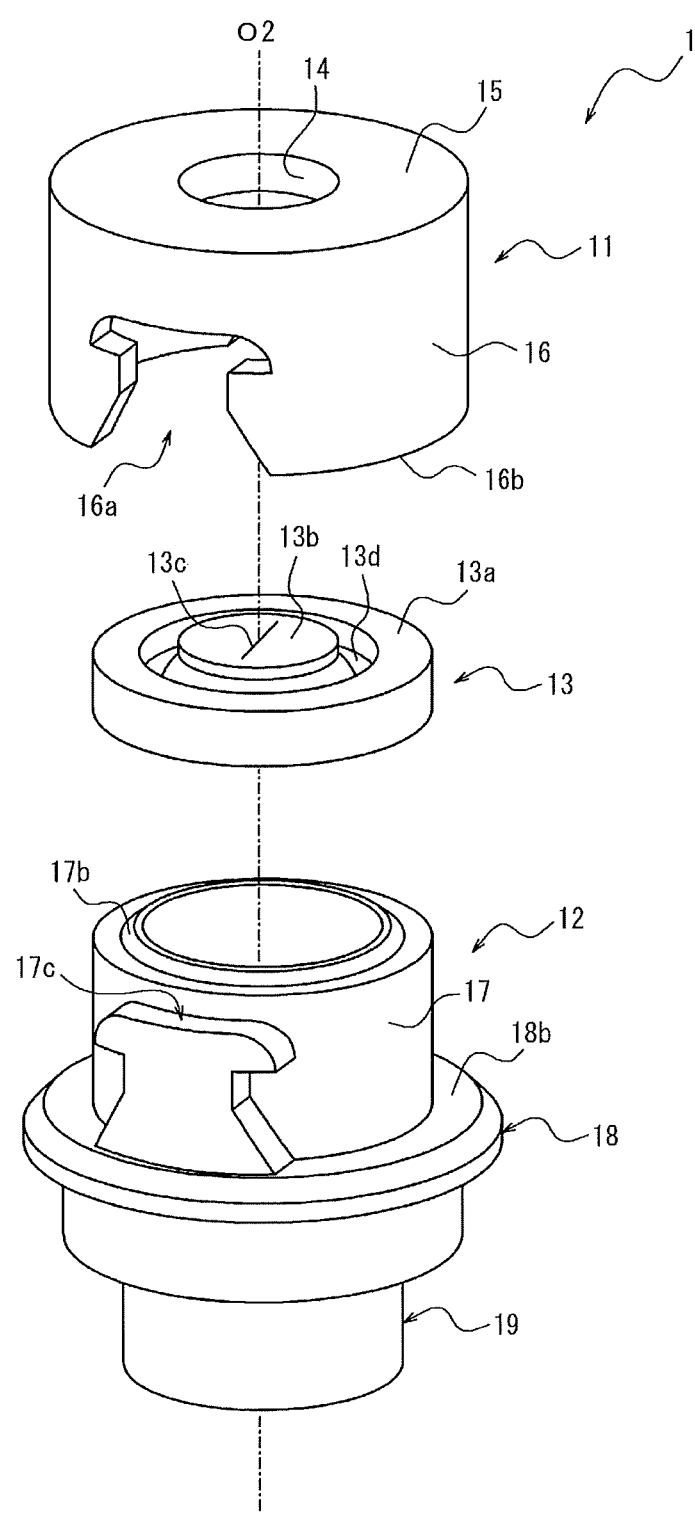
FIG. 2 is an exploded perspective view of the female connector illustrated in FIG. 1.
Figure 3:
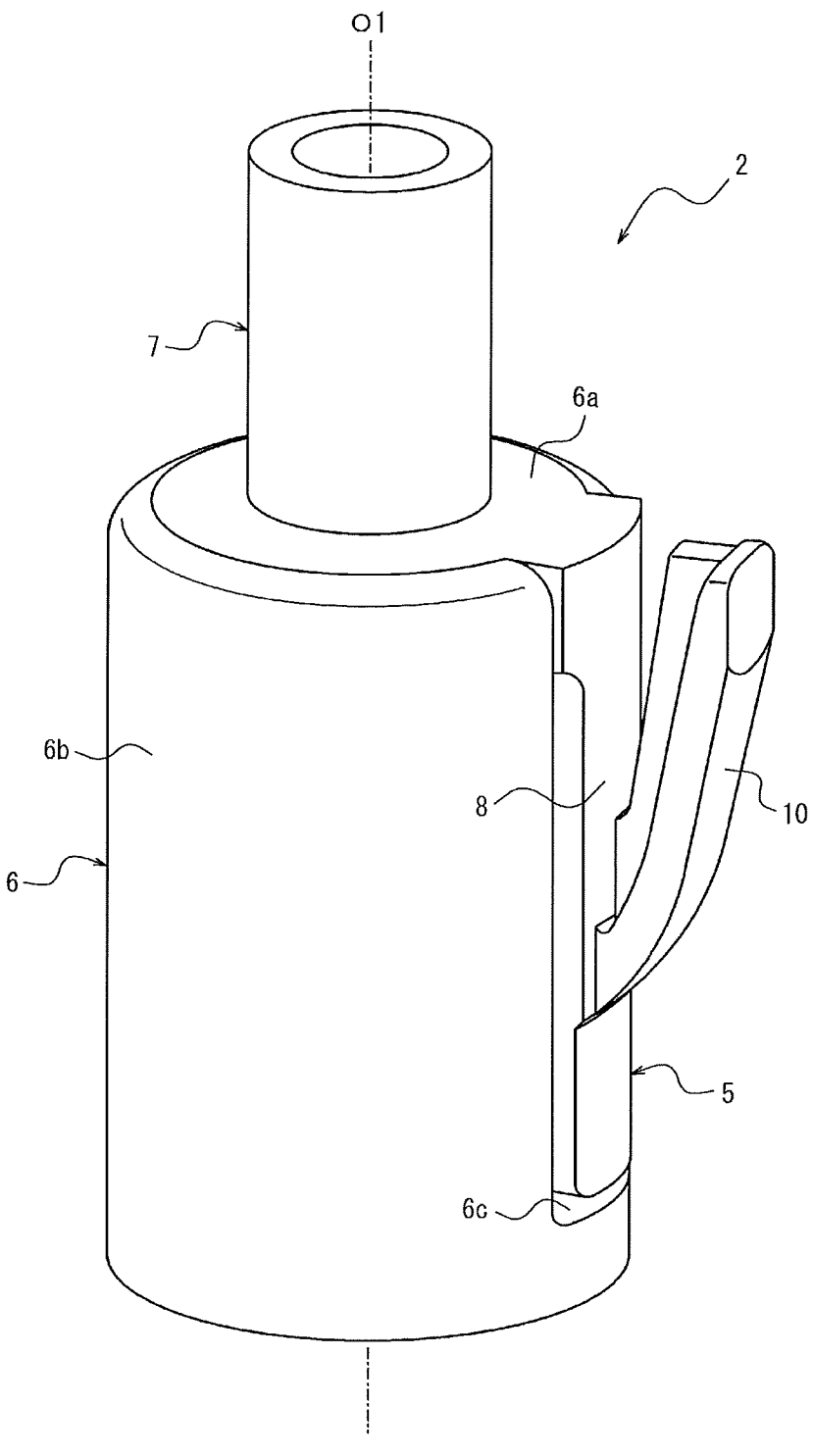
FIG. 3 is a perspective view of a male connector connectable to the female connector illustrated in FIG. 1.
Figure 4:
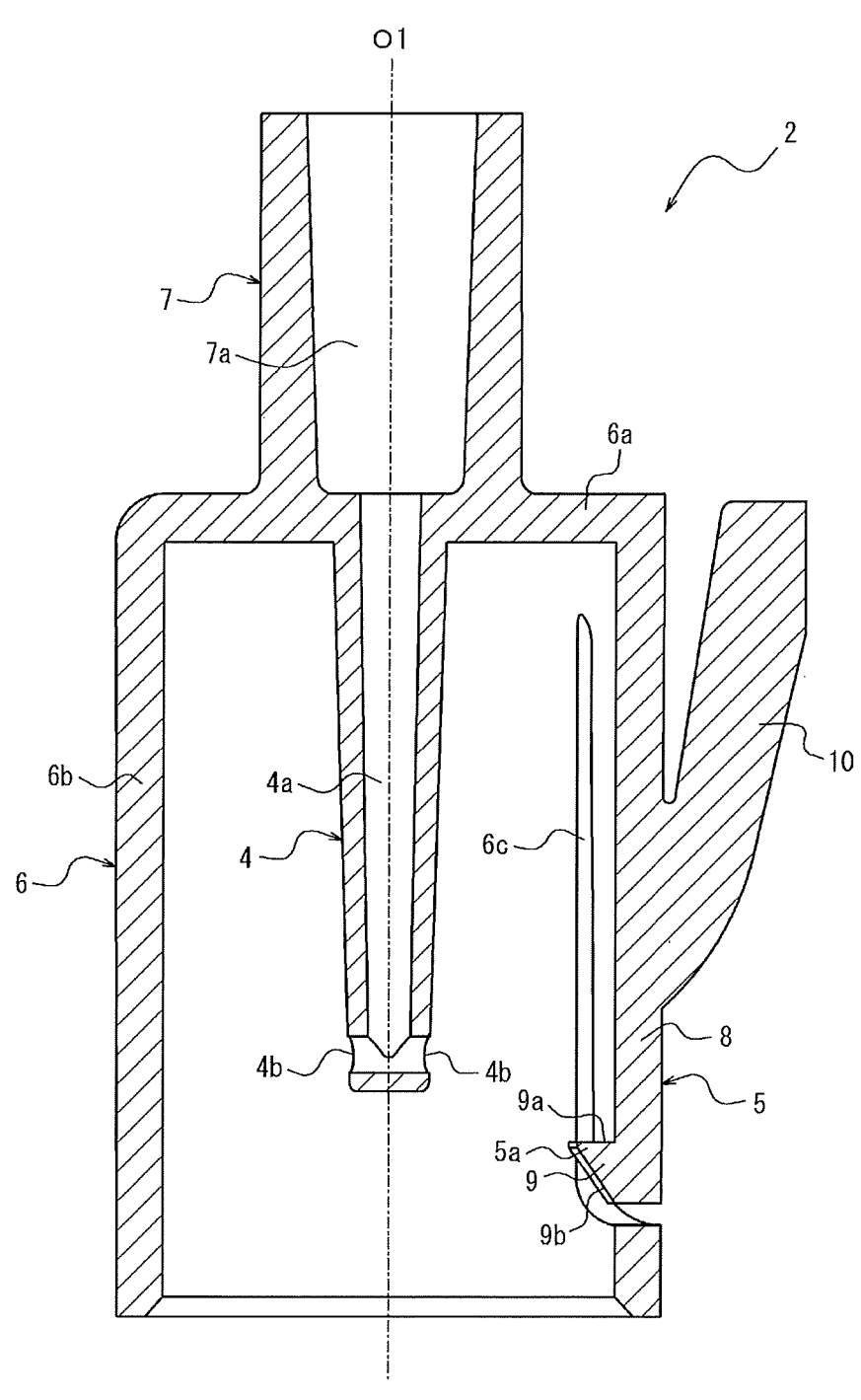
FIG. 4 is a cross-sectional view of the male connector illustrated in FIG. 3.
Figure 5:
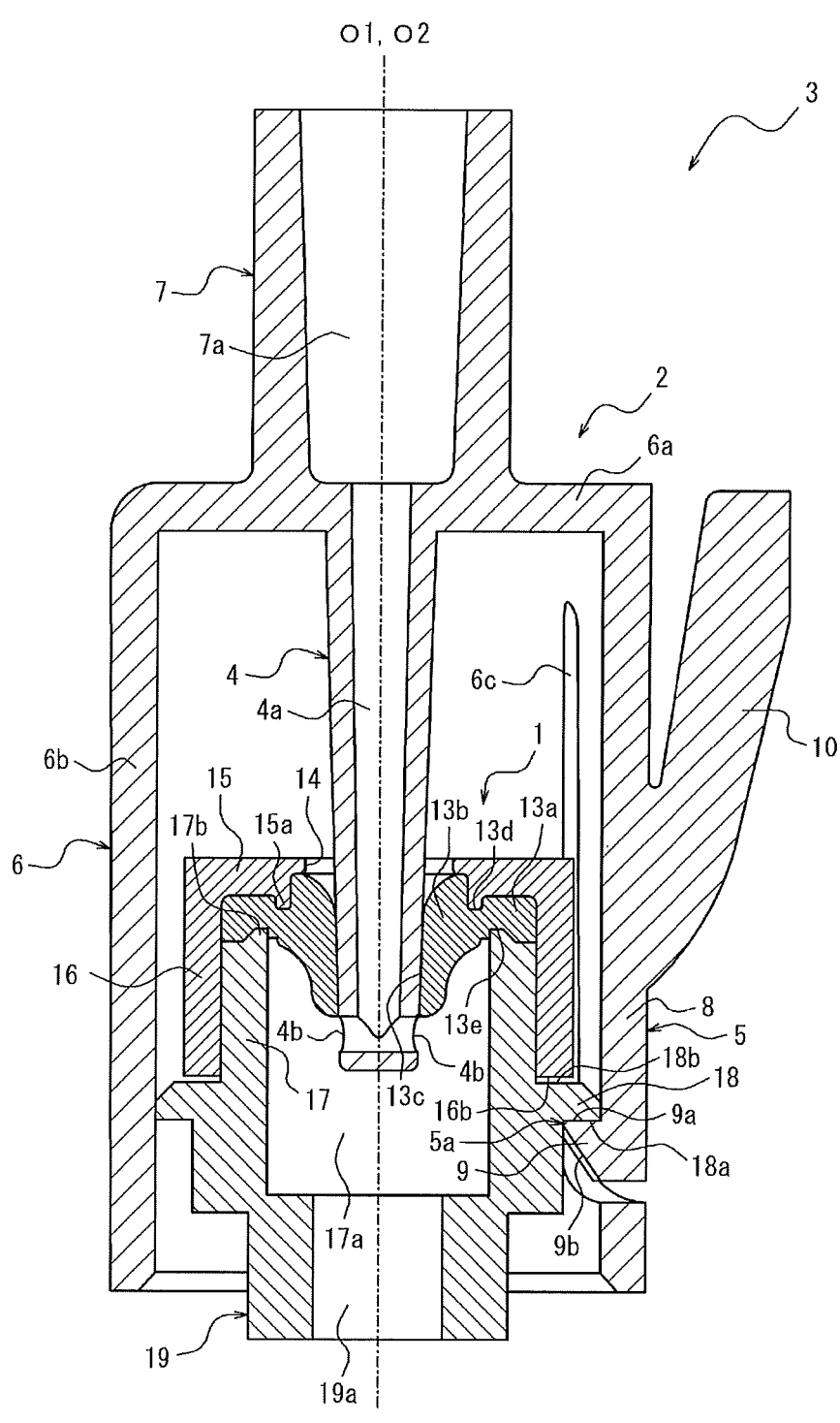
FIG. 5 is a cross-sectional view of the male connector illustrated in FIG. 3 being in a locked state when the male connector is connected to the female connector illustrated in FIG. 1.

The female connector 1 according to the first embodiment illustrated in FIGS. 1, 2, and 5 is connectable to the male connector 2 illustrated in FIGS. 3 to 5. The female connector 1 and the male connector 2 are included in a connector set 3. The connector set 3 is used to connect medical tubes, syringes, and other medical devices used in a feeding line (not illustrated) that delivers drug solutions, blood, and other fluids into the body from the outside of the body or from the body to the outside of the body for infusion, blood transfusion, and dialysis. The feeding line using the connector set 3 is, for example, an infusion line that delivers fluids into the body from the outside of the body.

As illustrated in FIGS. 3 to 5, the male connector 2 includes the channel connection 4, a lock claw 5, a cover 6, and a first tube connection portion 7. The male connector 2 is an integrated molded article including synthetic resin.

The channel connection portion 4 has a hollow rod shape that defines a first channel 4a inside. More specifically, the channel connection portion 4 has a cylindrical shape with a bottom, centered on the first axis O1, having a diameter that gradually reduces downward, and having two through holes 4b penetrating the distal end of the channel connection portion 4 in the radial direction.

The lock claw 5 includes a cantilevered arm 8 extending downward from a fixed end and a lock projection 9 protruding inward in the radial direction from a lower end (free end) of the arm 8. The lock projection 9 includes a horizontal upper surface 9a including an inner peripheral edge having an arc-shape in a top view and a tapered lower surface 9b gradually inclined downward and outward in the radial direction from the inner peripheral edge having an arc-shape in a top view. The inner peripheral edge of the upper surface 9a and an inner peripheral edge of the lower surface 9b form a tapered lock claw tip 5a.

An operating lever 10 leads to an outer peripheral surface of the arm 8. The operating lever 10 extends in a direction inclined upward and outward in the radial direction from an intermediate portion of the outer peripheral surface of the arm 8 in the up-and-down direction.

The cover 6 has a horizontal roof 6a and a cylindrical outer wall 6b. The outer wall 6b extends from an outer peripheral edge of the roof 6a, centered on the first axis O1. The roof 6a leads to the proximal end of the channel connection portion 4. The arm 8 of the lock claw 5 has an upper end leading to the outer wall 6b. The outer wall 6b has a cutout 6c, and the arm 8 is placed inside the cutout 6c.

The first tube connection portion 7 has a cylindrical shape centered on the first axis O1. The first tube connection portion 7 has a lower end leading to an upper surface of the roof 6a. The first tube connection portion 7 has an inner peripheral surface that defines a first tube connection channel 7a communicating with the first channel 4a of the channel connection portion 4. To the first tube connection portion 7, a medical tube is connected.

As illustrated in FIGS. 1, 2, and 5, the female connector 1 includes the cap 11, the housing 12, and a valve 13. The cap 11 and the housing 12 are casted products including synthetic resin. The valve 13 is a casted product including an elastic material such as rubber and elastomer.

The cap 11 includes the top wall 15 provided with an opening 14 that allows insertion of the channel connection 4 of the male connector 2 and a peripheral wall 16 extending from an outer peripheral edge of the top wall 15. The opening 14 has a circular shape in a top view. The top wall 15 has an annular shape in a top view. The top wall 15 has a lower surface provided with a first supporting protrusion 15a extending continuously or intermittently in the circumferential direction and protruding downward. The peripheral wall 16 includes two fitted portions 16a having a cutout opened downward and facing each other across the second axis O2. The peripheral wall 16 has a cylindrical shape centered on the second axis O2.

The housing 12 includes a cylindrical wall 17, an engaging protrusion 18, and a second tube connection portion 19.

The cylindrical wall 17 has an inner peripheral surface that defines a second channel 17a. The cylindrical wall 17 has an upper surface provided with a second supporting protrusion 17b extending continuously or intermittently in the circumferential direction and protruding upward. The cylindrical wall 17 has an outer peripheral surface including fitting portions 17c that respectively fit in the two fitted portions 16a of the cap 11 to fix the cap 11 to the housing 12. The two fitting portions 17c are disposed above the engaging protrusion 18, facing each other across the second axis O2. Each of the fitting portions 17c (and the fitted portions 16*a*) has a T-shape in side view. The outer peripheral surface of the cylindrical wall 17 has a cylindrical shape.

The engaging protrusion 18 protrudes from the outer peripheral surface of the cylindrical wall 17 and forms a lower surface 18*a* that is to be engaged with the upper surface 9*a* of the lock projection 9 of the lock claw 5 in order to connect the male connector 2 to the female connector 1 and put the male connector 2 in a locked state (that is, in a connected state).

Figure 6:
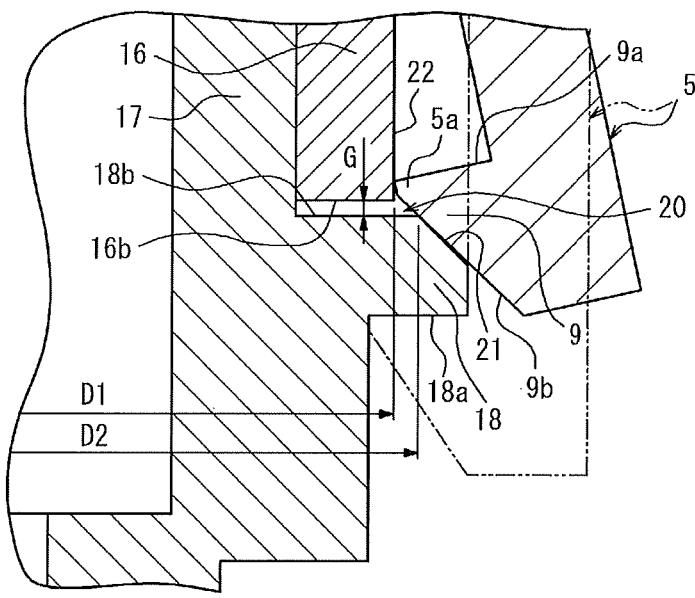
FIG. 6 is a view for describing the movement of a lock claw when the locked state illustrated in FIG. 5 is released.

As illustrated in FIG. 6, a boundary 20 is formed between an upper surface 18*b* of the engaging protrusion 18 and a lower end face 16*b* of the peripheral wall 16 of the cap 11. At the boundary 20, a gap G may be formed due to dimensional accuracy or assembly accuracy of each component.

In the boundary 20, the lower end face 16*b* of the peripheral wall 16 has an outer diameter D1 less than an outer diameter D2 of the upper surface 18*b* of the engaging protrusion 18. In addition, the engaging protrusion 18 has an outer peripheral surface including an enlarged diameter portion 21 having a tapered surface with a diameter increasing downward from the boundary 20. The peripheral wall 16 has an outer peripheral surface including a fixed diameter portion 22 that has a constant outer diameter extending upward from the boundary 20. The outer peripheral surface of the engaging protrusion 18 has a fixed outer diameter in the circumferential direction. A lower end of the enlarged diameter portion 21 has an outer diameter equal to an inner diameter of the cover 6.

As illustrated in FIGS. 1 and 5, for example, the second tube connection portion 19 has a cylindrical shape centered on the second axis O2. The second tube connection portion 19 has an upper end leading to a lower end of the cylindrical wall 17. The second tube connection portion 19 has an inner peripheral surface that defines a second tube connection channel 19*a* communicating with the second channel 17*a* of the cylindrical wall 17. To the second tube connection portion 19, a medical tube is connected.

As illustrated in FIGS. 1, 2, and 5, the valve 13 includes a sandwiched portion 13*a*, a partition 13*b*, and a penetration portion 13*c*. The sandwiched portion 13*a* is sandwiched by the top wall 15 and the cylindrical wall 17. The partition 13*b* has the penetration portion 13*c* or a slit shaped into a straight line in a top view. The penetration portion 13*c* is placed within the opening 14 in a top view and penetrates the valve 13 in the up-and-down direction. The partition 13*b* has a disk shape centered on the second axis O2. The sandwiched portion 13*a* has an annular shape leading to an outer peripheral edge of the partition 13*b*.

The valve 13 has an upper surface including an upper annular groove 13*d* extending along an inner peripheral edge of the sandwiched portion 13*a*. The first supporting protrusion 15*a* of the cap 11 is buried in the upper annular groove 13*d*. The valve 13 has a lower surface including a lower annular groove 13*e* extending along the inner peripheral edge of the sandwiched portion 13*a*. The second supporting protrusion 17*b* of the housing 12 is buried in the lower annular groove 13*e*.

The partition 13*b* closes one end of the second channel 17*a* of the cylindrical wall 17 when the male connector 2 is not connected to the female connector 1 (that is, in an unconnected state). In addition, when the engagement between the lock claw 5 and the engaging protrusion 18 causes a locked state, the penetration portion 13*c* of the partition 13*b* is penetrated by the channel connection 4 portion of the male connector 2 as illustrated in FIG. 5, thereby communicating the first channel 4*a* and the second channel 17*a*. In the locked state, the second axis O2, or the central axis of the peripheral wall 16 of the cap 11, substantially coincides with the first axis O1, or the central axis of the channel connection 4 portion.

When the male connector 2 is connected to the female connector 1, the lock claw tip 5*a* of the lock claw 5 of the male connector 2 is required to be elastically displaced in the radial direction by a radial width of the upper surface 9*a* of the lock projection 9. Because the outer peripheral surface of the engaging protrusion 18 has the enlarged diameter portion 21, the lock claw tip 5*a* moving downward is gradually displaced outward in the radial direction along the enlarged diameter portion 21. Accordingly, the male connector 2 is smoothly connected and put into a locked state (see the dash-dot-dot line in FIG. 6). Furthermore, when the male connector 2 is connected to the female connector 1, the female connector 1 is guided by an inner peripheral surface of the outer wall 6*b* of the cover 6. The locked state is maintained by a contact between the inner peripheral surface of the outer wall 6*b* of the cover 6 and the outer peripheral surface of the engaging protrusion 18.

In this embodiment, because the outer peripheral surface of the engaging protrusion 18 has a fixed outer diameter over the circumferential direction, the lock claw 5 is engaged with the engaging protrusion 18 at any position in the circumferential direction. Accordingly, there is no need to provide a structure for regulating a rotational position of the female connector 1 in the circumferential direction relative to the male connector 2, which enables a simple structure and connecting operation.

In order to release the locked state, the operating lever 10 is operated to displace a distal end of the arm 8 of the lock claw 5 outward in the radial direction to disengage the lock claw 5 and the engaging protrusion 18, and in this state, the male connector 2 is moved upward relative to the female connector 1.

Figure 7:
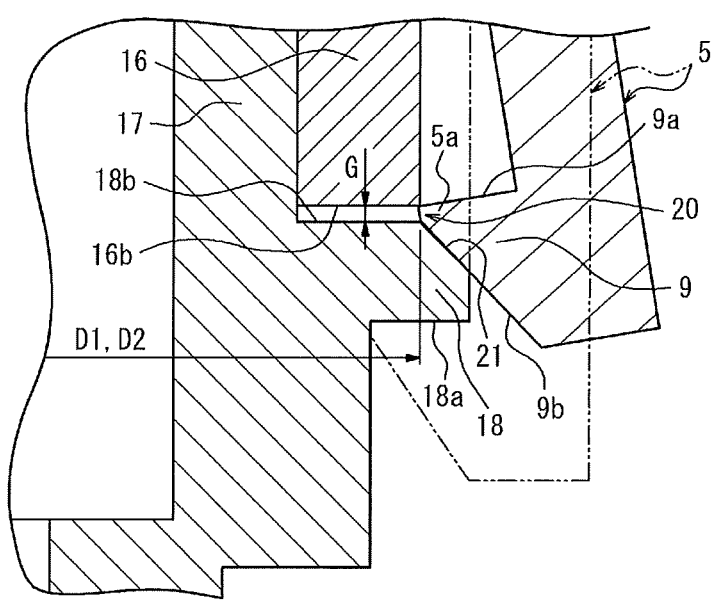
FIG. 7 is a view for describing the movement of a lock claw when a locked state is released in Comparative Example where a lower end face of a peripheral wall and an upper surface of the engaging protrusion have an equal outer diameter at a boundary.

As in Comparative Example illustrated in FIG. 7, in a case where the lower end face 16*b* of the peripheral wall 16 has an outer diameter D1 equal to an outer diameter D2 of the upper surface 18*b* of the engaging protrusion 18 at the boundary 20, when the locked state is released by unintended external forces or the like, the lock claw tip 5*a* may be engaged with the gap G at the boundary 20 as indicated by the solid line in FIG. 7. This state may be maintained even though it is not a normal connected state. Particularly, when the channel connection portion 4 has the through holes 4*b* penetrating the distal end in the radial direction as in this embodiment, the through holes 4*b* may be closed by the partition 13*b* of the valve 13.

However, it is difficult to discern such an abnormal connected state by appearance. Using connectors in this state may hinder intended fluid transfusion and cause a serious situation.

By contrast, in this embodiment, as illustrated in FIG. 6, the outer diameter D1 of the lower end face 16*b* of the peripheral wall 16 of the cap 11 is less than the outer diameter D2 of the upper surface 18*b* of the engaging protrusion 18 at the boundary 20. This makes it possible to prevent the lock claw tip 5*a* of the lock claw 5 of the male connector 2 from engaging with the boundary 20 (more specifically, with the lower end face 16*b* of the peripheral wall 16).

In addition, because the outer peripheral surface of the peripheral wall 16 has the fixed diameter portion 22 having a constant outer diameter extending upward from the boundary 20, it is possible to prevent the lock claw tip 5*a* from engaging with the outer peripheral surface of the peripheral wall 16 around the boundary 20 and from causing an abnormal connected state similar to the above situation.

Figure 8:
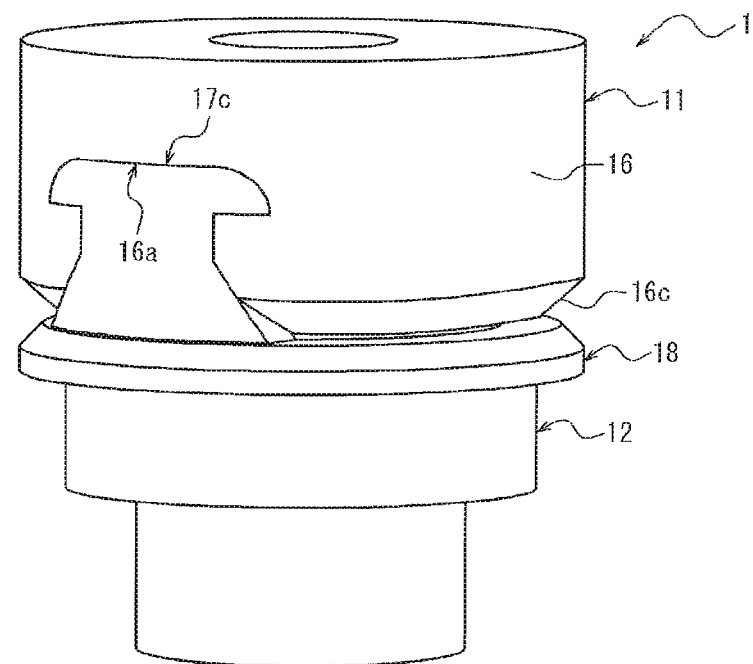
FIG. 8 is a perspective view of a female connector according to a second embodiment.
Figure 9:
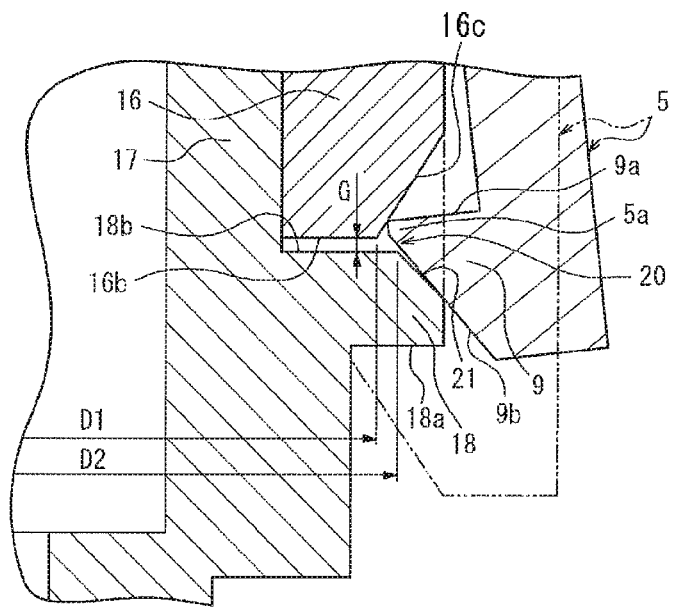
FIG. 9 is a view for describing the movement of a lock claw when the male connector illustrated in FIG. 3 connected to the female connector illustrated in FIG. 8 is unlocked.

In the first embodiment, the outer peripheral surface of the peripheral wall 16 include the fixed diameter portion 22. In a second embodiment, as illustrated in FIGS. 8 and 9, the outer peripheral surface of the peripheral wall 16 may include a tapered lower edge 16c having a diameter gradually increasing upward from the boundary 20. Even with such a configuration, it is possible to prevent the lock claw tip 5a from engaging with the outer peripheral surface of the peripheral wall 16 around the boundary 20 and to prevent an abnormal connected state similar to the above situation.

Figure 10:
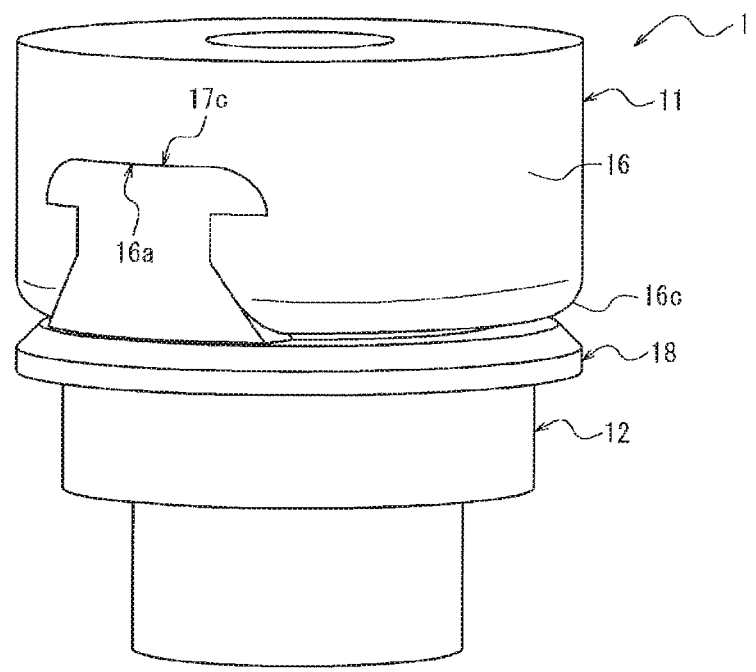
FIG. 10 is a perspective view of a female connector according to a third embodiment.
Figure 11:
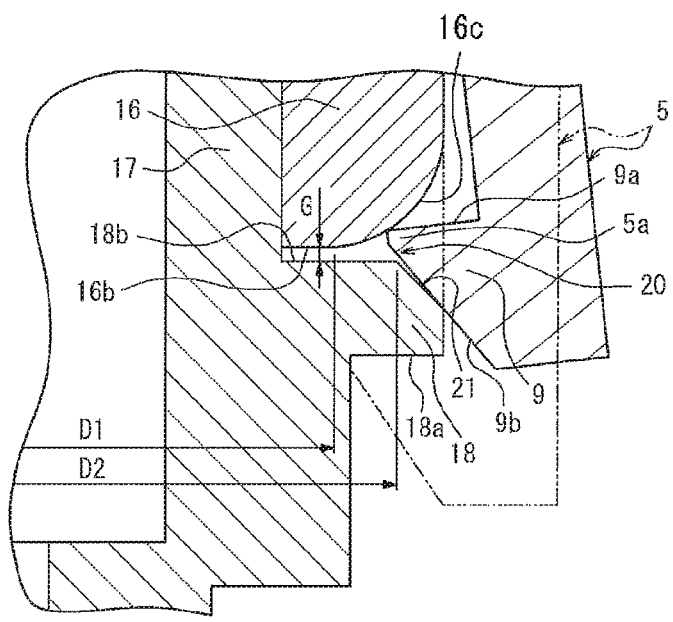
FIG. 11 is a view for describing the movement of a lock claw when the male connector illustrated in FIG. 3 connected to the female connector illustrated in FIG. 10 is unlocked.

Furthermore, in a third embodiment as illustrated in FIGS. 10 and 11, the outer peripheral surface of the peripheral wall 16 may include a protruding curved lower edge 16c having a diameter gradually increasing upward from the boundary 20. Even with such a configuration, it is possible to prevent the lock claw tip 5a from engaging with the outer peripheral surface of the peripheral wall 16 around the boundary 20 and to prevent an abnormal connected state similar to the above situation.

In each of the embodiments, in order to further prevent the lock claw tip 5a from being engaged with the gap G at the boundary 20, the shape of the lock claw tip 5a in a longitudinal cross section including the first axis O1 may be changed to a more rounded shape (for example, a shape including an arc). In each of the embodiments, in order to further prevent the engagement between the lock claw tip 5a and the gap G at the boundary 20, the lower surface 9b of the lock projection 9 may have a protruding curved shape gradually inclined downward and outward in the radial direction from the inner peripheral edge instead of having a tapered surface.

The embodiments are examples of this disclosure, and the following modifications may be employed.

The male connector 2 may have any configuration as long as the male connector 2 includes the lock claw 5 and the channel connection portion 4 having a hollow rod shape that defines the first channel 4a inside. The number and arrangement of the through holes 4b in the channel connection portion 4 are changed according to the situation. The through holes 4b may penetrate the channel connection portion 4 in the up-and-down direction. The structure of the portion leading to the proximal end of the channel connection portion 4 to form the channel communicating with the first channel 4a is not limited to the first tube connection portion 7 and may be changed in various ways. The shape and arrangement of the operating lever 10 are changed according to the situation. The lock claw 5 is not limited to one operated by the operating lever 10. The lock claw 5 is not limited to one including the cantilevered arm 8. The male connector 2 is not limited to one including the cover 6.

The male connector 2 may be of closed-type including an elastic valve that closes the channel connection portion 4 in an unconnected state and exposes the distal end of the channel connection portion 4 in a connected state. The male connector 2 may have two or more lock claws 5.

The cap 11 may have any configuration as long as the cap 11 includes the top wall 15 provided with the opening 14 that allows insertion of the channel connection portion 4 and the peripheral wall 16 extending from the outer peripheral edge of the top portion 15. The opening 14 is not limited to one having a circular shape in a top view.

The housing 12 may have any configuration as long as the housing 12 includes the cylindrical wall 17 having the inner peripheral surface that defines the second channel 17a and the engaging protrusion 18 protruding from the outer peripheral surface of the cylindrical wall 17 to form the lower surface 18a to be engaged with the lock claw 5 in order to connect the male connector 2 to the female connector 1 and put the male connector 2 into a locked state. The structure of the portion leading to the lower end of the cylindrical wall 17 to form the channel communicating with the second channel 17a is not limited to the second tube connection portion 19 and may be changed in various ways.

The valve 13 may have any configuration as long as the valve 13 includes the sandwiched portion 13a sandwiched between the top wall 15 and the cylindrical wall 17 and the penetration portion 13c placed within the opening 14 in a top view and penetrating the valve 13 in the up-and-down direction. The sandwiched portion 13a is not limited to one having an annular shape in a top view. The penetration portion 13c is not limited to a slit having a straight line shape in a top view and may be, for example, an X-shaped or Y-shaped slit in a top view or other shapes.

The female connector 1 may have any configuration as long as the female connector 1 includes the cap 11, the housing 12, and the valve 13 and has the following configuration: the boundary 20 is formed between the upper surface 18b of the engaging protrusion 18 and the lower end face 16b of the peripheral wall 16, the outer diameter D1 of the lower end face 16b of the peripheral wall 16 is less than the outer diameter D2 of the upper surface 18b of the engaging protrusion 18 at the boundary 20, and the outer peripheral surface of the engaging protrusion 18 has the enlarged diameter portion 21 with a diameter increasing downward from the boundary 20. The enlarged diameter portion 21 is not limited to one having a tapered surface. The outer peripheral surface of the engaging protrusion 18 is not limited to one having a fixed outer diameter over the circumferential direction. The female connector 1 is not limited to one including the cap 11 and the housing 12 that are fixed by the fitted portions 16a and the fitting portions 17c.

What is claimed is:

1. A female connector configured to connect to a male connector, the male connector comprising a lock claw and a channel connection portion having a hollow rod shape that defines a first channel in the channel connection portion, the female connector comprising:

a cap;

a housing; and a valve; wherein:

the cap comprises:

a top wall comprising an opening configured to receive the channel connection portion, and a peripheral wall extending from an outer peripheral edge of the top wall;

the housing comprises:

a cylindrical wall having an inner peripheral surface that defines a second channel, and an engaging protrusion protruding from an outer peripheral surface of the cylindrical wall to form a lower surface configured to engage with the lock claw to connect the male connector to the female connector and put the male connector into a locked state; and the valve comprises:

a sandwiched portion sandwiched between the top wall and the cylindrical wall, and a penetration portion located in the opening in a top view and penetrating the valve in an up-and-down direction;

the engaging protrusion and the peripheral wall form a boundary between a flat upper surface of the engaging protrusion and a lower end face of the peripheral wall;

an outer diameter of the lower end face of the peripheral wall is less than an outer diameter of the flat upper surface of the engaging protrusion; and the engaging protrusion has an outer peripheral surface including a tapered surface that extends directly from the flat upper surface of the engaging protrusion, the tapered surface having a diameter that increases downward from the flat upper surface of the engaging protrusion.

2. The female connector according to claim 1, wherein the peripheral wall has an outer peripheral surface including a fixed diameter portion having a constant outer diameter extending upward from the boundary.

3. The female connector according to claim 1, wherein the peripheral wall has an outer peripheral surface including a lower edge having a tapered surface or a protruding curved surface with a diameter that increases upward from the boundary.

4. The female connector according to claim 1, wherein the outer peripheral surface of the engaging protrusion has a fixed outer diameter in a circumferential direction.

5. A connector set comprising:

a male connector comprising:

a lock claw, and a channel connection portion having a hollow rod shape that defines a first channel in the channel connection portion; and a female connector configured to connect to the male connector, the female connector comprising:

a cap;

a housing; and a valve; wherein:

the cap comprises:

a top wall comprising an opening configured to receive the channel connection portion, and a peripheral wall extending from an outer peripheral edge of the top wall;

the housing comprises:

a cylindrical wall having an inner peripheral surface that defines a second channel, and an engaging protrusion protruding from an outer peripheral surface of the cylindrical wall to form a lower surface configured to engage with the lock claw to connect the male connector to the female connector and put the male connector into a locked state; and the valve comprises:

a sandwiched portion sandwiched between the top wall and the cylindrical wall, and a penetration portion located in the opening in a top view and penetrating the valve in an up-and-down direction;

the engaging protrusion and the peripheral wall form a boundary between a flat upper surface of the engaging protrusion and a lower end face of the peripheral wall;

an outer diameter of the lower end face of the peripheral wall is less than an outer diameter of the flat upper surface of the engaging protrusion; and the engaging protrusion has an outer peripheral surface including a tapered surface that extends directly from the flat upper surface of the engaging protrusion, the tapered surface having a diameter that increases downward from the flat upper surface of the engaging protrusion.

6. The connector set according to claim 5, wherein the peripheral wall has an outer peripheral surface including a fixed diameter portion having a constant outer diameter extending upward from the boundary.

7. The connector set according to claim 5, wherein the peripheral wall has an outer peripheral surface including a lower edge having a tapered surface or a protruding curved surface with a diameter that increases upward from the boundary.

8. The connector set according to claim 5, wherein the outer peripheral surface of the engaging protrusion has a fixed outer diameter in a circumferential direction.

9. A method comprising:

providing a male connector comprising:

a lock claw, and a channel connection portion having a hollow rod shape that defines a first channel in the channel connection portion; and providing a female connector comprising:

a cap;

a housing; and a valve; wherein:

the cap comprises:

a top wall comprising an opening configured to receive the channel connection portion, and a peripheral wall extending from an outer peripheral edge of the top wall;

the housing comprises:

a cylindrical wall having an inner peripheral surface that defines a second channel, and an engaging protrusion protruding from an outer peripheral surface of the cylindrical wall to form a lower surface configured to engage with the lock claw; and the valve comprises:

a sandwiched portion sandwiched between the top wall and the cylindrical wall, and a penetration portion located in the opening in a top view and penetrating the valve in an up-and-down direction;

the engaging protrusion and the peripheral wall form a boundary between a flat upper surface of the engaging protrusion and a lower end face of the peripheral wall;

an outer diameter of the lower end face of the peripheral wall is less than an outer diameter of the flat upper surface of the engaging protrusion; and the engaging protrusion has an outer peripheral surface including a tapered surface that extends directly from the flat upper surface of the engaging protrusion, the tapered surface having a diameter that increases downward from the flat upper surface of the engaging protrusion; and connecting the male connector to the female connector such that the lower surface of the engaging protrusion engages with the lock claw, thereby putting the male connector into a locked state.

* * * * *